(12) United States Patent
Criswell et al.

(10) Patent No.: US 11,354,546 B2
(45) Date of Patent: Jun. 7, 2022

(54) INSECT SINGULATION AND CLASSIFICATION

(71) Applicant: Verily Life Sciences LLC, South San Francisco, CA (US)

(72) Inventors: Victor Criswell, Burlingame, GA (US); Peter Massaro, San Carlos, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 16/859,405

(22) Filed: Apr. 27, 2020

(65) Prior Publication Data

US 2020/0349397 A1 Nov. 5, 2020

Related U.S. Application Data

(60) Provisional application No. 62/843,092, filed on May 3, 2019.

(51) Int. Cl.
*G06K 9/62* (2022.01)
*A01K 67/00* (2006.01)
(Continued)

(52) U.S. Cl.
CPC ............ *G06K 9/6267* (2013.01); *A01K 67/00* (2013.01); *G06T 7/0002* (2013.01); *G06V 10/25* (2022.01)

(58) Field of Classification Search
CPC .... G06K 9/6267; G06K 9/3233; A01K 67/00; G06T 7/0002; B07C 5/363; B07C 5/02
See application file for complete search history.

(56) References Cited

U.S. PATENT DOCUMENTS

| 5,594,654 A * | 1/1997 | Shuman | ............... A01K 67/033 700/213 |
| 7,496,228 B2 * | 2/2009 | Landwehr | ............. A01M 1/026 382/165 |

(Continued)

FOREIGN PATENT DOCUMENTS

| CN | 104850836 | 8/2015 |
| CN | 106997475 | 8/2017 |

(Continued)

OTHER PUBLICATIONS

Landwehr et al., "Logistic Model Trees", Machine Learning, Kluwer Academic Publishers-Plenum Publishers, 2005, pp. 161-205.
(Continued)

*Primary Examiner* — John B Strege
(74) *Attorney, Agent, or Firm* — Kilpatrick Townsend & Stockton LLP

(57) ABSTRACT

An insect sortation system can track movement of insects along a predefined pathway. The insect sortation system includes a puff-back system for moving insects toward an inlet of the pathway and a puff-forward system for moving insects toward an outlet of the pathway. An overhead imaging system captures images of the insects at one or more locations along the pathway. Once imaged, the insect may be classified into a category (e.g., sex category, species category, size category, etc.) using a variety of different classification approaches including, for example, an industrial vision classifier and/or a machine learning classifier. Once classified, the insects can be directed to various chambers for subsequent processing.

35 Claims, 6 Drawing Sheets

(51) Int. Cl.
 *G06T 7/00* (2017.01)
 *G06V 10/25* (2022.01)

(56) References Cited

U.S. PATENT DOCUMENTS

| | | | |
|---|---|---|---|
| 7,849,032 | B1 | 12/2010 | Campos et al. |
| 8,025,027 | B1* | 9/2011 | Morales-Ramos .. A01K 67/033 119/6.5 |
| 8,269,842 | B2 | 9/2012 | Wang et al. |
| 8,478,052 | B1 | 7/2013 | Yee et al. |
| 9,633,306 | B2 | 4/2017 | Liu et al. |
| 9,668,699 | B2 | 6/2017 | Georgescu et al. |
| 9,730,643 | B2 | 8/2017 | Georgescu et al. |
| 9,786,270 | B2 | 10/2017 | Senior et al. |
| 9,830,526 | B1 | 11/2017 | Lin et al. |
| 9,990,558 | B2 | 6/2018 | Lin et al. |
| 10,007,866 | B2 | 6/2018 | Criminisi et al. |
| 10,019,654 | B1 | 7/2018 | Pisoni |
| 10,278,368 | B1* | 5/2019 | Peeters .............. A01K 67/033 |
| 2017/0273290 | A1* | 9/2017 | Jay .................. G06K 9/00771 |
| 2017/0273291 | A1* | 9/2017 | Yoo ...................... A01M 1/06 |
| 2017/0316281 | A1 | 11/2017 | Criminisi et al. |
| 2018/0121764 | A1 | 5/2018 | Zha et al. |
| 2018/0206473 | A1 | 7/2018 | Massaro et al. |
| 2018/0279598 | A1* | 10/2018 | Hur ...................... A01M 1/106 |
| 2019/0104719 | A1* | 4/2019 | Guo ..................... A01M 3/005 |
| 2020/0281164 | A1* | 9/2020 | Lepek ................ A01K 67/033 |
| 2020/0349668 | A1 | 11/2020 | Desnoyer et al. |

FOREIGN PATENT DOCUMENTS

| | | |
|---|---|---|
| CN | 106733701 | 5/2018 |
| GB | 2300480 | 11/1996 |
| WO | 2019008591 | 1/2019 |

OTHER PUBLICATIONS

Larios et al., "Automated Insect Identification through Concatenated Histograms of Local Appearance Features: Feature Vector Generation and Region Detection for Deformable Objects", Machine Vision And Applications, vol. 19, No. 2, 2008, pp. 105-123.
International Application No. PCT/US2020/030127, "Invitation to Pay Additional Fees and, Where Applicable, Protest Fee", Sep. 4, 2020, 12 pages.
International Application No. PCT/US2020/030128, "Invitation to Pay Additional Fees and, Where Applicable, Protest Fee", Jul. 14, 2020, 18 pages.
Cheng et al., "3D Tracking Targets Via Kinematic Model Weighted Particle Filter", 2016 IEEE International Conference on Multimedia and Expo (ICME), Available online at https://www.researchgate.net/publication/307436501_3D_tracking_targets_via_kinematic_model_weighted_particle_filter, Jul. 11, 2016, pp. 1-6.
Kumar et al., "Robust Insect Classification Applied to Real Time Greenhouse Infestation Monitoring", Available Online at https://www.semanticscholar.org/paper/Robust-Insect-Classification-Applied-to-Real-Time-Kumar-Martin/71f9c50ec4bdf66f5b6365fd158ce541ede4f2fd?p2df, Dec. 31, 2010, pp. 1-4.
International Application No. PCT/US2020/030128, International Search Report and Written Opinion, dated Oct. 20, 2020, 24 pages.
Rustia et al., "A Real-time Multi-Class Insect Pest Identification Method Using Cascaded Convolutional Neural Networks", 9th International Symposium on Machinery and Mechatronics for Agriculture and Biosystems Engineering (ISMAB), May 28, 2018, pp. 1-6.
International Application No. PCT/US2020/030127 , International Search Report and Written Opinion, dated Nov. 20, 2020, 17 pages.
Application No. CN202090000536.2, Office Action, dated Mar. 16, 2022, 2 pages (Machine Translation).

* cited by examiner

INSECT SINGULATION AND CLASSIFICATION

CROSS REFERENCE TO RELATED APPLICATIONS

The present application claims the benefit of U.S. Provisional Patent Application No. 62/843,092 entitled "Insect Singulation And Classification" and filed on May 3, 2019, the disclosure of which is hereby incorporated by reference in its entirety.

Additionally, the present application is related to U.S. Non-provisional patent application Ser. No. 16/859,397 entitled "Predictive Classification Of Insects" filed concurrently, which claims the benefit of U.S. Provisional Patent Application No. 62/843,080 entitled "Predictive Classification Of Insects" and filed on May 3, 2019, the disclosure of which is hereby incorporated by reference in its entirety.

BACKGROUND

As part of a Sterile Insect Technique (SIT) program, insects be may be classified as male or female and selectively sterilized before being released into the wild. Such programs may be implemented to minimize or eliminate insect-borne diseases and/or to manage insect populations in certain areas. Depending on the program, classification and sterilization may be performed at one or more stages of insect development. For example, adult male and female insects may be classified based on sex prior to one sex being sterilized.

BRIEF SUMMARY

Various examples are described including systems, methods, and devices relating to singulating and sorting adult insects.

One general aspect includes an insect sortation system, including: an insect pathway defining an interior volume and having an inlet and an outlet, where an approach zone of the insect pathway is defined adjacent the inlet, a classification zone of the insect pathway is defined adjacent the outlet, and a singulation zone of the insect pathway is defined between the approach zone and the classification zone. The insect sortation system also includes a puff back region defined adjacent the inlet. The insect sortation system also includes a puff forward region defined adjacent the outlet. The insect sortation system also includes an imaging system disposed adjacent the insect pathway and configured to image insects on the insect pathway.

Another general aspect includes an insect sortation method, including: receiving image data from an imaging system disposed adjacent to an insect pathway, the image data representative of one or more insects on the insect pathway. The insect sortation method also includes determining positions of one or more insects with respect to a plurality of zones of the insect pathway based on the image data. The insect sortation method also includes causing movement, by a puff system, of at least one insect of the one or more insects based on a position of the at least one insect with respect to the plurality of zones. The insect sortation system may be computer-implemented. Other examples of this aspect include corresponding computer systems, apparatus, and computer programs recorded on one or more computer storage devices, each configured to perform the actions of the method.

Another general aspect includes a non-transitory computer-readable storage device including computer-executable instructions that, when executed by a computer system, cause the computer system to perform operations including: receive image data from an imaging system disposed adjacent to an insect pathway, the image data representative of one or more insects on the insect pathway. The operations also include determine positions of one or more insects with respect to a plurality of zones of the insect pathway based on the image data. The operations also include causing movement, by a puff system, of at least one insect of the one or more insects based on a position of the at least one insect with respect to the plurality of zones.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
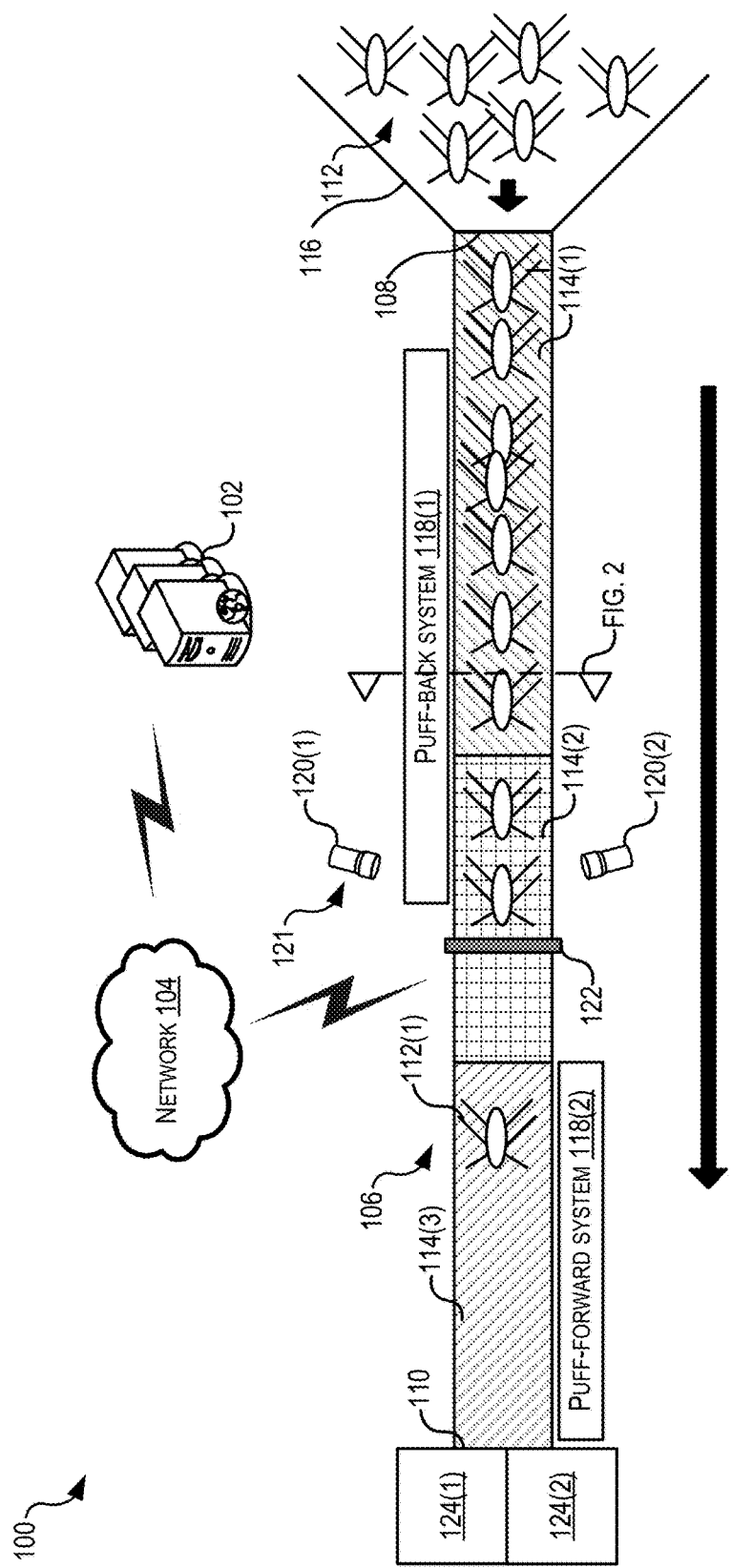
FIG. 1 illustrates a top view of an insect sortation system, according to at least one example.

Examples are described herein in the context of an insect sortation system and corresponding methods for singulating and classifying adult stage insects, and in particular adult stage mosquitoes of particular species. Those of ordinary skill in the art will realize that the following description is illustrative only and is not intended to be in any way limiting. For example, the systems and processes described herein can be used to singulate and classify mosquitoes and insects in other stages and/or other species. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, an insect sortation system is configured to manage movement of insects along a predefined pathway in a manner that enables an imaging system time to capture images of the insects and a computing device to classify the insects based on the images. To this end, the insect sortation system includes an insect pathway or corridor in which insect such as mosquitoes walk single file in one direction from an inlet to an outlet. An overhead camera is positioned to view (and image) the insects as they walk on the insect pathway (e.g., the insect pathway may have a transparent ceiling). The system includes a puff-back system located adjacent the inlet. The puff-back system is configured to output a blast of air to drive insects toward the inlet. Further down the insect pathway, the system includes a puff-forward system located adjacent the outlet. The puff-forward system is configured out output a blast of air to drive insects toward the outlet. The puff systems can be selectively controlled to break up groups of insects and separate single insects from a group of insects, and to position insects in particular locations along the pathway.

The insect pathway is divided into multiple zones which correspond to functions that the system performs in the various zones. For example, after the inlet and adjacent the puff-back system, the insect pathway includes an approach zone. Adjacent the outlet and the puff-forward system, the insect pathway includes a classification zone. And finally, between these two zones, the insect pathway includes a singulation zone. The system, in some cases, includes a mechanical shutter located in the singulation zone. The shutter controls back pressure when the two puff systems are operating and holds back insects while a singulated insect is being classified.

The puff systems, the overhead camper, and the shutter are computer-controlled to separate and singulate the insects as they move through the insect pathway, and to image the insects. Rules for operating the puff systems, the shutter, the overhead camera, and other components depend on in which zone the insect is located. For example, the rules can define time thresholds for how long an insect can remain in a particular zone and/or quantity thresholds for how many insects can be present at any one time in a particular zone.

Figure 2:
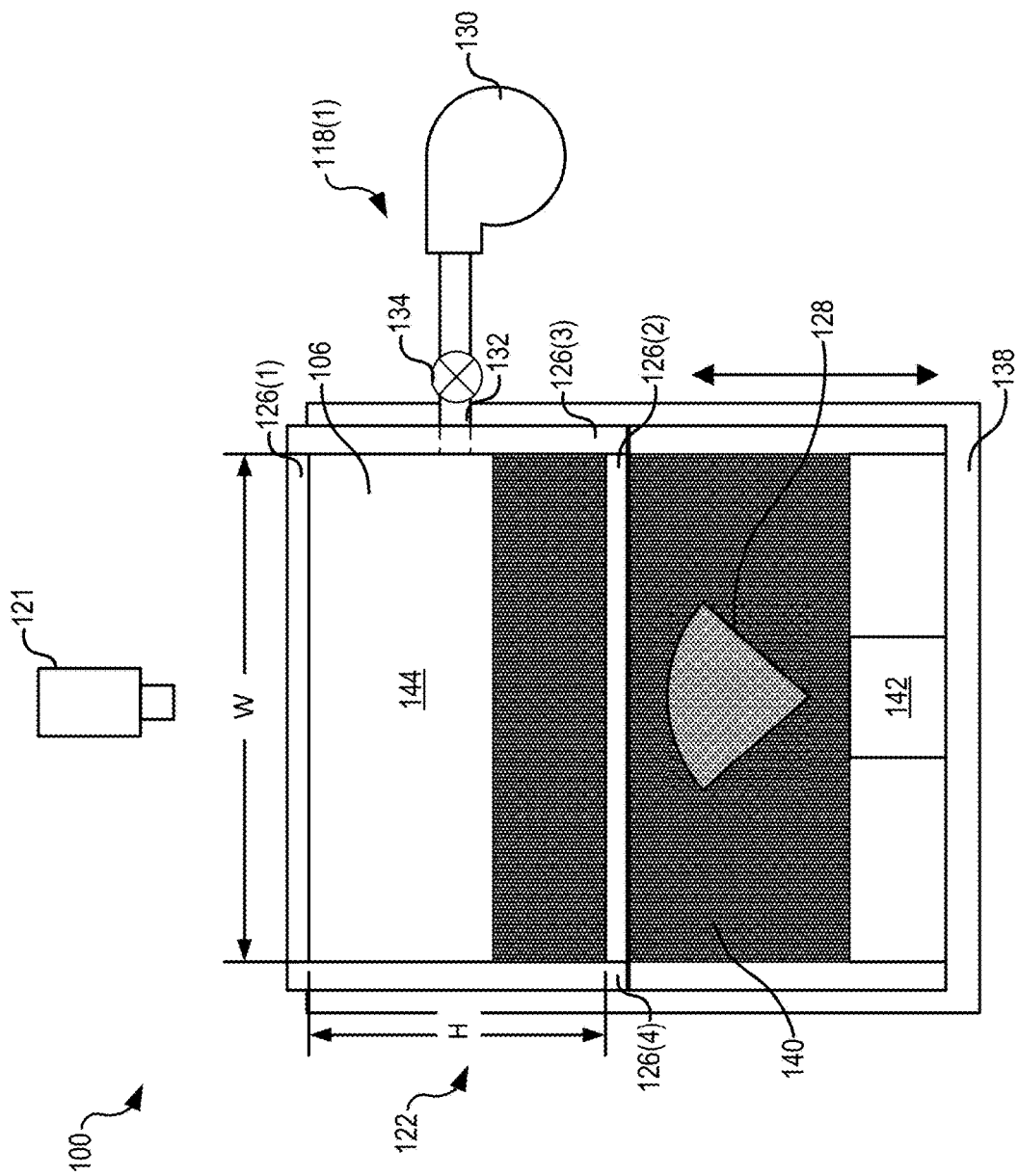
FIG. 2 illustrates a section view of the insect sortation system of FIG. 1, according to at least one example.

FIGS. 1 and 2 respectively illustrate a top view and a section view of an insect sortation system 100 for singulating and separating insects based on a determined classification, according to at least one example. The insect sortation system 100, which is illustrated in a simplified form, can be used to singulate, count, classify, and sort a population of insects based on any suitable characteristics. For example, the characteristics can include sex, size, species, genus, health, and the like. The insect sortation system 100 includes any suitable combination of chambers, paths, doors, blowers, lights, actuators, and any other mechanical or electrical means to singulate the population of insects in a manner that enables counting, classifying, and sorting. These components of the insect sortation system 100 may be actuated by instructions provided by the computing device 102 via the network 104. In this manner, the computing device 102 may control the operation of the insect sortation system 100. The network 104 may be any suitable combination of wired, wireless, local, wide-area, cellular, and any other network for enabling device communication.

In some examples, one or more components of the insect sortation system 100 are connected to the computing device 102 via one or more hardware interfaces such as would be appropriate for the given component. Such interfaces may enable the computing device 102 to communicate with the components of the insect sortation system 100.

Turning now to the details of the insect sortation system 100, the system 100 includes an insect pathway 106 that includes an inlet 108 and an outlet 110. Generally, the insect pathway 106 provides a bounded path for guiding movement of insects 112 from the inlet 108 to the outlet 110 in the direction of the directional arrows in FIG. 1. As the insects 112 move along the insect pathway 106 different systems interact with the insects 112 to achieve the purposes described herein.

An end cross-sectional size of the insect pathway 106, as described with respect to FIG. 2, may be selected to correspond to an example insect that is being processed by the insect sortation system 100. For example, the insect pathway 106 may have a rectangular cross section defined by a height H and a width W. In some examples, W is greater than H. The value of H may be larger than an average height of a population of insects 112. The value of W may be larger than an average foot-to-foot exterior width of the population of insects 112 to be processed by the insect sortation system 100.

The insect pathway 106 is formed from a plurality sections 126 including a ceiling section 126(1), a floor section 126(2), and a pair of connecting wall sections 126(3), 126(4), which generally define a rectangular interior volume Generally, the insects 112 may walk through the interior volume along the floor section 126(2). Below the floor section 126(2) is disposed a lighting element 128 positioned and configured to shine light into the interior volume 144 of the insect pathway 106 to provide back-lighting for the imaging system 121. To achieve this function, the floor section 126(2) may be formed from a translucent material such as a translucent plastic or glass. Such backlighting may be desirable to improve the likelihood that the system can distinguish one insect from another and individual parts of an insect.

The ceiling section 126(1) may be formed from a transparent material to allow the overhead imaging system 121 to view the interior volume 144 without obstruction. In some examples, the ceiling section 126(1) is excluded. The pair of connecting wall sections 126(3), 126(4) may be formed from any suitable material, which may range from opaque to transparent. In some examples, using opaque material may encourage the insects 112 to move forward toward the outlet 110.

Figure 4:
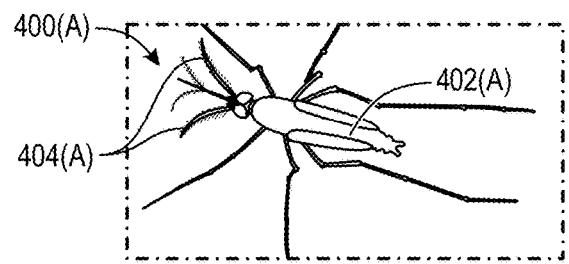
FIG. 4 illustrates example images of pairs of insects, according to at least one example.
Figure 4:
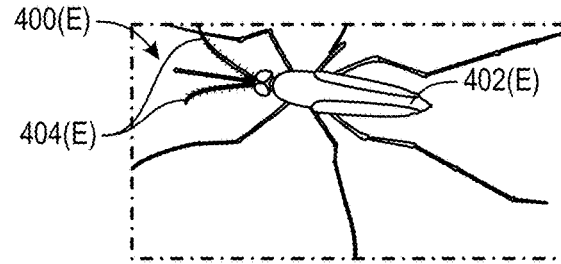
Figure 4:
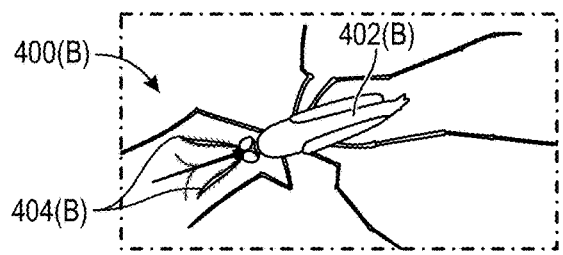
Figure 4:
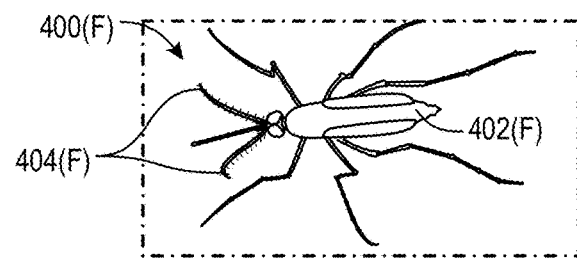
Figure 4:
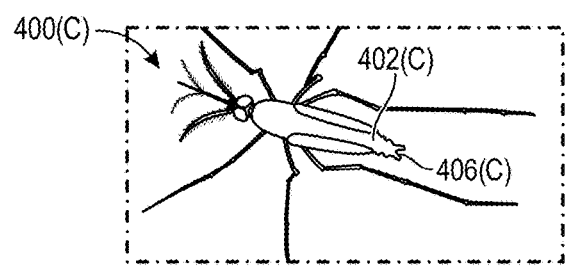
Figure 4:
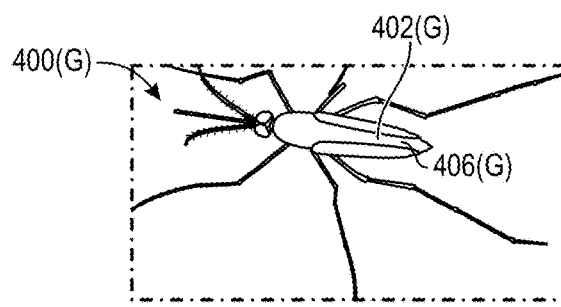
Figure 4:
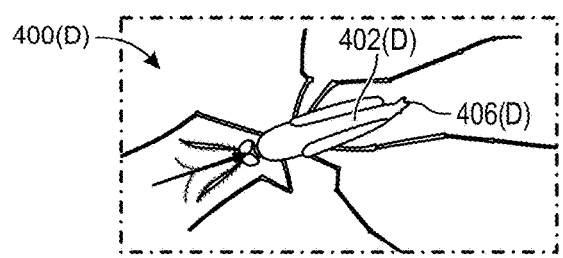
Figure 4:
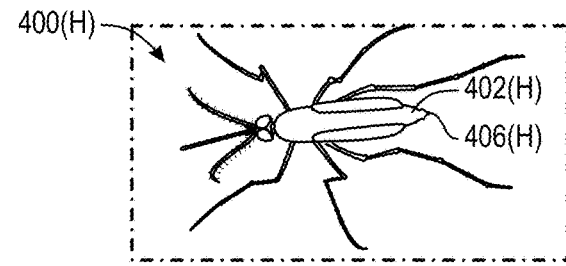

The insect pathway 106 is divided to define a plurality of zones 114(1)-114(N). Edges of the zones 114 may be physically demarcated in the insect pathway 106 and/or may be virtually demarcated, i.e., stored in by the computing device 102. Each zone 114 extends longitudinally along the insect pathway 106. The actions performed with respect to the insects 112 while on the insect pathway 106 may depend on which zone 114 the insect is located. These actions are defined by a set of rules which are implemented by a processor of the computing device 102. Examples of such rules and corresponding actions are described with reference to FIG. 4. While three zones 114 are illustrated, it should be understood that any suitable number of zones including more than three or less than three may be used.

Zone 114(1) is referred to as an approach zone. Zone 114(2) is referred to as a singulation zone. Zone 114(3) is referred to as a classification zone. The approach zone 114(1) begins at the inlet 108 and ends at a first edge of the singulation zone 114(2). The singulation zone 114(2) extends between the approach zone 114(1) and the classification zone 114(3). The classification zone 114(3) begins at a second edge of the singulation zone 114(2) and ends at the outlet 110.

The insect sortation system 100 also includes one or more puff systems such as a puff-back system 118(1) located at a puff-back region of the insect pathway 106 and a puff-forward system 118(2) located at a puff-forward region of the insect pathway 106. The puff systems 118 are in communication with, and in some examples, under control of the computing device 102. Generally, the puff systems 118 are configured to output small amounts or "puffs" of air into the insect pathway 106 to move the insects 112, e.g., toward the inlet 108 and/or toward the outlet 110. In some examples, the puff systems 118 puff the insects 112 in directions other than toward the inlet 108 and toward the outlet 110. While one puff-back system 118(1) and one puff-forward system 118(2) are illustrated, it should be understood that more than one of each may be used. For example, a puff-back system 118(1) may be placed on both sides of the insect pathway 106 (e.g., above and below the insect pathway 106 in the illustrated view). Similarly, a puff-forward system 118(2) may be placed on both sides of the insect pathway 106. In some examples, the puff systems 118 are positioned above and/or below the insect pathway 106 in addition to or instead of the side(s).

An example of the puff-back system 118(1) is illustrated in FIG. 2. Other puff systems 118 are omitted from FIG. 2 for purposes of clarity. The puff-back system 118(1) includes an air source 130 connected to a puff outlet 132. A control valve 134 is positioned between the air source 130 and a distal end of the puff outlet 132. The distal end of the puff outlet 132 extends into the interior volume 144. In some examples, more than one puff outlet 132 is included, which can be controlled by one control valve 134 using a manifold of puff outlets 132 disposed longitudinally along the pathway 106 or multiple control valves 134 each connected to a puff outlet 132. The use of multiple puff outlets 132 may enable more granular movement and singulation of insects. In operation, the air source 130, which is a pump, pressure vessel, or a pump in combination with a pressure vessel, increases pressure in the puff outlet 132 and the control valve 134 is selectively opened and closed to let the air escape via the distal end. In this manner, the puff-back system 118(1) puts out a "puff" of air. In some examples, the control valve 134 may be selectively opened and closed within a few milliseconds.

The insect sortation system 100 also includes an imaging system 121 including one or more imaging devices 120(1)-120(N) in communication with, and in some examples, under the control of the computing device 102. The imaging system 121 is configured to capture images of regions of interest within the insect pathway 106. In some examples, the field of view of the imaging system 121 covers the entire insect pathway 106, e.g., from the inlet 108 to the outlet 110. In this manner, the imaging system 121 may image the insects 112 at various positions along the insect pathway 106. Given the geometric sizing of the insect pathway 106, the insects 112 move generally in a single-file line along the insect pathway 106. Because of this, the imaging system 121 is configured to capture images of individual insects 112 as they move through the insect pathway 106.

The insect sortation system 100 also includes a shutter 122 in communication with, and in some examples, under the control of the computing device 102. The shutter 122 is positioned partway between the inlet 108 and the outlet 110. In this manner, the shutter 122 divides an interior volume 144 of the insect pathway 106 into a first compartment including the approach zone 114(1) and a portion of the singulation zone 114(2), and a second compartment including the classification zone 114(3) and a portion of the singulation zone 114(2). The shutter 122 is operable between an open state and a closed state. In the open state, the insects 112 can move between the two compartments. In the closed state, the insects 112 are prevented from moving between the two compartments.

An example of the shutter 122 is illustrated in FIG. 2. As illustrated, the shutter 122 includes a frame 138 in which is held a door 140 and an actuator 142 operably connected to the door 140. In operation, the actuator 142 slides the door 140 within the frame 138 between the open state and the closed state. The door 140 of the shutter 122 may open top-to-bottom, bottom-to-top, or from either side in the insect pathway 106. In some examples, the shutter 122 includes more than one door 140, e.g., a plurality of angular doors that open and close in different directions. In FIG. 2, the door 140 is illustrated in a partially open state.

If an insect 112 remains in the shutter 122 greater than some predetermined threshold of time, the computing device 102 causes the puff-back system 118(1) to output an air blast to remove the insect 112 from the shutter 122.

Finally, the insect sortation system 100 also includes one or more sort chambers 124(1)-124(N). The sort chambers 124 are used to hold the insects 112 after they have been classified in the classification zone 114(3). Each of the sort chambers 124 can hold the insects 112 having different characteristics. In some examples, two sort chambers 124 are included. In other examples, a single sort chamber 124 is used and into which is directed insects 112 having a certain characteristic (e.g., sex equals male), while all other insects (e.g., sex equals not-male) are directed to a waste chamber. The insects 112 can be removed from the sort chambers 124 in any suitable way (e.g., using compressed air) and used for any suitable purpose (e.g., a SIT program).

As the components of the insect sortation system 100 have now been described, their respective functions will now be described. Additional functions will be described with reference to the corresponding flow chart(s). Generally, when a population of insects 112 first enters the insect pathway 106, information about the population can be obtained from the imaging system 121, and this information can be used to self-calibrate components of the insect sortation system 100. For example, the information may include the general size of the insects, size of legs, number of legs, etc., which may be used as a parameter to calibrate the imaging system 121, the shutter 122, the lighting element 128, and other components of the system 100.

As the insects enter the approach zone 114(1), the insects 112 begin to line up one-by-one within the insect pathway 106. For example, a population of insects 112 may move from a holding chamber via a funnel 116 and onto the approach zone 114(1) via the inlet 108. Given the size of the insect pathway 106, the insects 112 are constrained to line up front-to-back. However, in some cases, the insects 112 may get tangled, begin to bunch up, or otherwise crowd each other. The imaging system 121 captures images of the insects 112 as they move within the approach zone 114(1). Images may be sampled at a rate of 10 frames/second. In some examples, the sampling rate may be greater than or less than 10 frames/second. The computing device 102 processes the images using an object detection algorithm to determine positions of the insects 112. In some examples, their positions are determined with respect to the shutter 122. If the insects 112 are crowding each other, are not moving, or are moving too fast, the computing device 102 instructs the puff-back system 118(1) to output a puff of air to blow back the insects 112, e.g., toward the inlet 108. These are examples are rules that can be implemented in the approach zone 114(1). This puff functions to separate the clump of insects 112 and, often times, results in separation of a single insect from the clump. A puff can be part of a puff sequence, with a first puff being rather gentle and the intensity increasing with subsequent puffs.

As the insects continue through the approach zone 114(1) and into the singulation zone 114(2), the imaging system 121 continues to image them and the computing device 102 continues to track their positions. Within the singulation zone 114(2), the insects 112 are singulated such that only one insect 112 at a time passes through the shutter 122 and into the classification zone 114(3). For example, as illustrated, the insect 112(1) alone is located in the classification zone 114(3) and has been separated from the remaining insects in zones 114(1) and 114(2).

Opening and closing of the shutter 122 is coordinated with the operation of the puff-back and puff-forward systems 118 to ensure that only one insects passes through the shutter 122 at any one time. For example, as a leading insect approaches the shutter 122, the puff-back system 118(1) may be operated to blow back trailing insects. As soon as the leading insect passes through the shutter 122, the shutter 122 will be closed thereby preventing other insects from passing through. With the shutter 122 closed, the shutter 122 acts as a safety valve to keep other insects 112 from entering the classification zone 114(3) and existing the insect pathway 106. Additionally, with the shutter 122 closed, the shutter 122 controls back pressure when the puff systems 118 operate. For example, when the puff-forward system 118(2) operates, the closed shutter 122 prevents other insects 112 from being pulled toward the classification zone 114(3). Likewise, when the puff-backward system 118(1) operates, the closed shutter 122 prevents other insects 112 from being pulled back toward the inlet 108.

As the insect 112(1) continues through the singulation zone 114(2) and into the classification zone 114(3), the imaging system 121 continues to image the insect 112(1) and the computing device 102 continues to track its position. In some examples, instead of or in addition to position tracking, while in the classification zone 114(2), the imaging system 121 and the computing device 102 also perform classification. This can include using an object detection algorithm to detect parts of the insect 112(1), measure these parts (as appropriate), identify characteristics of these parts, and based on this information determine a classification of the insect 112(1). For example, as described with reference to FIG. 4, features of the insect 112(1) may be used to classify the insect 112(1) as a male or female.

Figure 3:
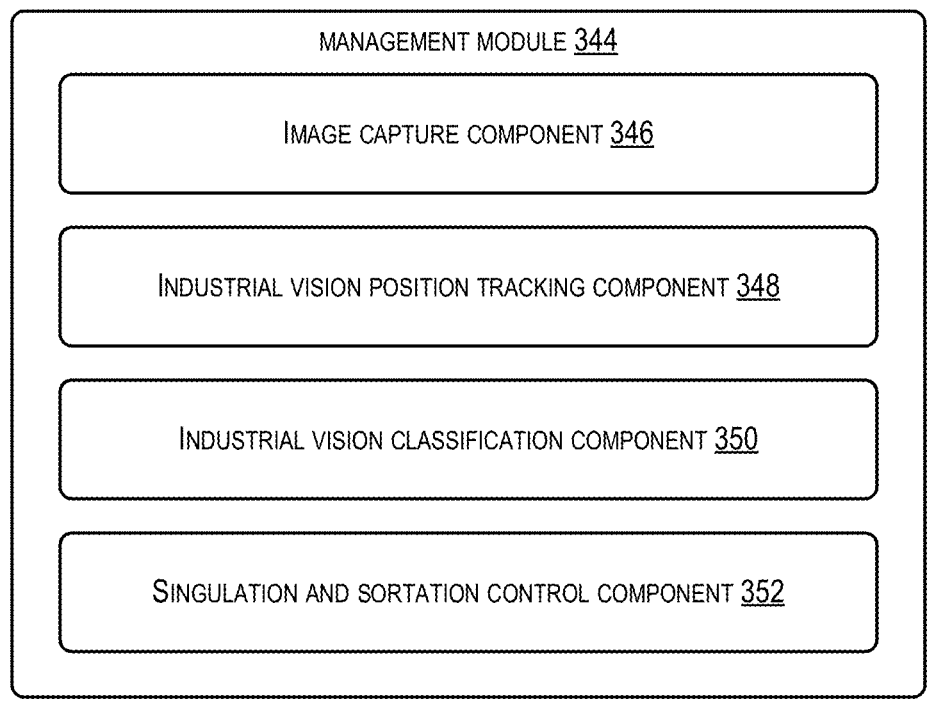
FIG. 3 illustrates an example device including a management module for managing aspects of the insect sortation system of FIG. 1, according to at least one example.

FIG. 3 illustrates an example device 300 including a management module 344 for managing aspects of the insect sortation system 100, according to at least one example. The device 300 includes any suitable combination of hardware, software, and/or firmware configured to implement the functionality described with reference to the management module 344. The computing device 102 is an example of the device 300. In some examples, the device 300 is implemented in the computing device 102. Generally, the management module 344 includes an image capture component 346, an industrial vision position tracking component 348, an industrial vision classification component 350, a singulation and sortation control component 352, and a validation component 354.

Turning now the image capture component 346, the image capture component 346 is configured to control the function of the imaging system 121. This may include instructing the imaging system 121, including which of the imaging devices 120, regarding when to capture images, how frequently, and the like. The image capture component 346 may store information (e.g., in the form of metadata) in association with the images. Such information can include timestamps, location data, build and version data, unique image identifiers, and the like.

The industrial vision position tracking component 348 is configured to use data obtained by the imaging system 121 or other sensor system (e.g., position sensors) to identify and track the position of objects such as insects 112 in the images. In some examples, the industrial vision position tracking component 348 executes any suitable edge-detection and/or blob detection algorithm.

Initially, the object may be segmented from the background by subtracting the image taken by the imaging device shortly before the object is present. The object can be compared to a known object in the field of view to determine a two-dimensional location. In some examples, a one-dimensional distance is used. For example, a distance between an insect 112 and the shutter 122 may be determined.

The industrial vision classification component 350 is configured to use data obtained by the imaging system 121 to extract features of the insects 112 and classify the insects based on these features. In some examples, the industrial vision classification component 350 executes any suitable feature-based object detection and extraction algorithm.

For example, once the objects are detected and segmented, features can be extracted from the segmented object. In some examples, these features may include, but are not limited to: size of the object, shape of the object, visual similarity to a known example, color of the object, texture of the object, the same type of features extracted from sub-regions of the object, and the same type of features extracted from successive images of the same object.

The features may be combined together using a manually designed set of rules, or they can be combined using a decision tree (e.g., Bayesian or boosted). Decision trees are lightweight machine learning algorithms that require less data to train to their maximum potential than a full machine learning classifier but can often achieve better performance than hand selected rules. The resulting trained decision tree may then be implemented as a sequence of if/then statements in any coding platform.

In the particular implementation of the industrial vision classification component 350 that classifies mosquitoes based on sex, a mosquito walks in front of an imaging device (e.g., the imaging system 121) running at 5-10 frames per second. As described with respect to images 400(A)-400(H) in FIG. 4, for each frame, the system looks for the mosquito's body 402. If the body 402 is found, then if the body is too large, it is rejected as females are larger than males. See, for example, male mosquito bodies 402(A)-402(D) in images 400(A)-400(D) compared with female mosquito bodies 402(E)-402(H) in images 400(E)-400(H). If the body 402 is small enough, then the system looks for bushy antennae 404 of the males mosquito as well as identifying claspers 406 at the rear. The antenna 404(A) and 404(B) of the males are much bushier than the antenna 404(E) and 404(F) of the females. The claspers 406(C) and 1240606(D) of the males are more dull and, in some examples, look like there are two distal structures as compared to the claspers 406(G) and 406(H) of the females. If the claspers 406 are positively identified, the image is classified as male. If both antennae 404 are found, then the image is also classified as male. For an insect to be classified as male in this example, all frames with a valid body 402 found must be identified as male and at least three images must be used before the mosquito reaches a specific point along the lane. If not enough images are acquired, the mosquito is pushed back with air in order to acquire more images. The industrial vision classification component 350 then outputs a classification and a confidence. In other examples, different techniques, requirements, or thresholds may be used. For example, rather than requiring all frames to have an identifiable body, a lower threshold may be used. Similarly, a different threshold number of images than three may be employed.

The singulation and sortation control component 352 is configured to control components such as the puff systems 118, the shutter 122, and other automated components of the insect sortation system 200. For example, the singulation and sortation control component 352 may control the operation of the puff systems 118 and the shutter 122 based on feedback from the imaging system 121 and/or other sensors present in the system 100 (e.g., proximity sensors, weight sensors, and the like configured to output information useable to determine a location of an insect within the system 100). The singulation and sortation control component 352 is also configured to direct an insect to a particular chamber 124 based on a classification made while the insect is in the classification zone 114(3).

Figure 5:
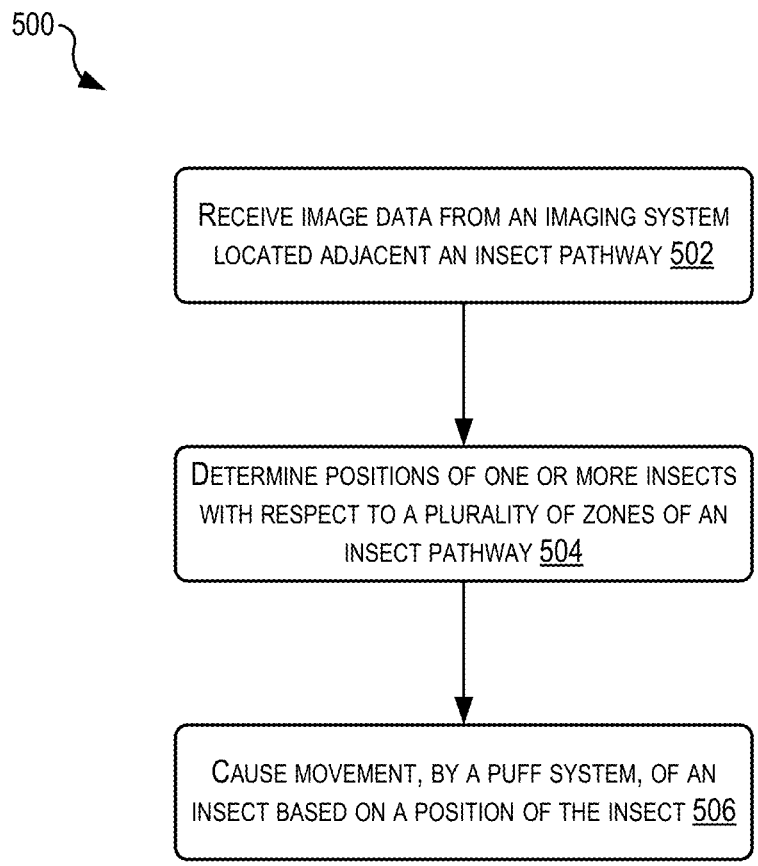
FIG. 5 illustrates an example flow chart depicting process for classifying insects, according to at least one example.

FIG. 5 illustrates an example flow diagram showing process 500, according to at least one example. This process, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer readable storage medium, for example, in the form of a computer program including a plurality of instructions executable by one or more processors.

FIG. 5 illustrates an example flow chart depicting the process 500 for classifying insects, according to at least one example. The process 500 is performed by the management module 344 (FIG. 3) executing in the computing device 102 (FIG. 1). The process 500 is executed within the context of the insect sortation system 100.

The process 500 begins at block 502 by the computing device 102 receiving image data from an imaging system located adjacent an insect pathway such as the insect pathway 106. In some examples, the image capture component 346 (FIG. 3) executing in the computing device 102 receives the image data from the imaging system 121 (FIG. 1). The image data is representative of one or more insects on the insect pathway. In some examples, the computing device 102 instructs the imaging system 121 to capture the image data prior to the computing device 102 receiving the image data. In some examples, the imaging system 121 begins capturing the image data based on some triggering event. For example, a sensor may detect when insects are first introduced into the insect pathway 106, e.g., via the inlet 108. Sensor data from this sensor may be used to trigger the imaging system 121 to begin capturing images of the insect pathway 106.

In some examples, the imaging system 121 includes one or more imaging devices 120 such as cameras. For example, a pair of cameras may obtain the image data. In other examples, a first camera (or a first set of cameras) is dedicated to obtaining image data for tracking insects (e.g., a position tracking imaging system configured to capture images of the insects for position tracking of the insects along the insect pathway 106), and a second camera (or a second set of cameras) is dedicated to obtaining image data for classifying insects (e.g., an insect classification imaging system configured to capture images of the insects for classification of the insects within the classification zone 114(3). In this example, the first camera may have a field of view that includes the approach zone 114(1) and at least a portion of the singulation zone 114(2), and the second camera may include a field of view that includes the classification zone 114(3).

At block 504, the process 500 includes the computing device 102 determining positions of the one or more insects with respect to a plurality of zones of the insect pathway 106. In some examples, the industrial vision position tracking component 348 (FIG. 3) executing in the computing device 102 performs the block 504. Determining the positions is based on the image data received at the block 502.

At block 506, the process 500 includes the computing device 102 causing movement, by a puff system (e.g., 118), of an insect of the one or more insects based on a position of the insect. In some examples, the singulation and sortation control component 352 (FIG. 3) executing in the computing device 102 performs the block 506. The position of the insect may be determined with respect with respect to the plurality of zones of the insect pathway.

The plurality of zones may include the approach zone 114(1) located adjacent the inlet 108 of the insect pathway 106, the classification zone 114(3) located adjacent the outlet 110 of the insect pathway 106, and the singulation zone 114(2) located between the approach zone 114(2) and the classification zone 114(3).

The puff system 118 may include one or more puff outlets 132 extending into the insect pathway 106, an air source 130 that provides an air flow to the one or more puff outlets 132, and a control valve 134 disposed between the air source 130 and the one or more puff outlets 132. The computing device 102 may control the control valve 134 to moderate the air flow to the one or more puff outlets 132. In some examples, the computing device 102 controls the control valve 134 in each puff system 118 based on the positions of the insects to separate a single insect from the insects when the insects are in the singulation zone 114(2).

In some examples, performing the block 506 includes the computing device 102 determining that insect has remained within the approach zone 114(1) beyond a maximum threshold amount of time (e.g., a few seconds), and instructing the puff-back system 118(1) to puff a burst of air that moves the insects toward the inlet 108. This puff of air may irritate the insects and cause them to start moving again. This determining may be based on additional image data or the same image data.

In some examples, performing the block 506 includes the computing device 102 determining that a quantity of insects within the approach zone 114(1) exceeds a maximum threshold quantity of insects for the approach zone 114(1), and instructing the puff-back system 118(1) to puff a burst of air that moves the insects toward the inlet 108. For example, the insects may be grouped together which may have resulted in a tangle of insects, and this puff of air may break up the tangle and allow the insects to start walking down the insect pathway 106 again. This determining may be based on additional image data or the same image data.

In some examples, performing the block 506 includes the computing device 102 determining that the insect has remained within the classification zone 114(3) beyond a maximum threshold amount of time, and instructing the puff-forward system 118(2) to puff a burst of air that moves the insects toward the outlet 110. This puff of air may cause the insect to move toward the outlet and out of the classification zone 114(3). Once out of the classification zone 114(3), a next insect can be moved into the classification zone 114(3) for classification. This determining may be based on additional image data or the same image data.

In some examples, performing the block 506 includes the computing device 102 determining that insect has remained at a particular position within the classification zone 114(3) beyond a maximum threshold amount of time, and instructing the puff-forward system 118(1) to puff a burst of air that moves the insects toward the outlet 110. For example, to make a suitable classification, a suitable number of images of the insect in different positions may be required. Thus, if the computing device 102 determines from the image data that the insect has not moved between a number of image frames, the computing device 102 may instruct the puff-forward system 118(2) to puff a burst of air at the insect. In some examples, this burst of air is gentle, but sufficient to encourage the insect to beginning moving again. If a suitable number of images of the insect in different positions are not obtained by the time the insect walks out of the classification zone 114(3), the insect may be rejected as not being classified.

In some examples, performing the block 506 includes the computing device 102 isolating the from the one or more other insects. For example, the computing device 102 can instruct the puff-back system 118(1) to push back the one or more other insects to allow the insect to pass through the shutter 122. Once through the shutter 122, the computing device 102 instructs the shutter 122 to close, thereby isolating the insect from the one or more other insects. In some examples, the puff-back system 118(1) is configured to isolate the insect from the one or more other insects without using the shutter 122.

In some examples, the imaging system 121 includes one or more imaging devices 120 such as cameras including multiple image sensors and/or a single image sensor. In this example, the process 500 additionally includes receiving additional image data from the imaging system 121 when the imaging system is located within the classification zone 114(3), identifying one or more characteristics of the one insect based on the additional image data, and classifying the images based on the one or more characteristics. The industrial vision classification component 350 (FIG. 3) may identify the characteristics and classify the images based on the characteristics. In this example, the one or more characteristics may include a head, a body area, a body length, a tail, or an antenna. In this example, classifying the insect may include classifying the insect based on insect sex, insect health, insect species, insect genus, or insect size.

In some examples, the process 500 further includes the computing device 102 causing movement, by the puff system 118, of the insect based on classifying the insect. This can include directing the insect into one of the sort chambers 124.

Figure 6:
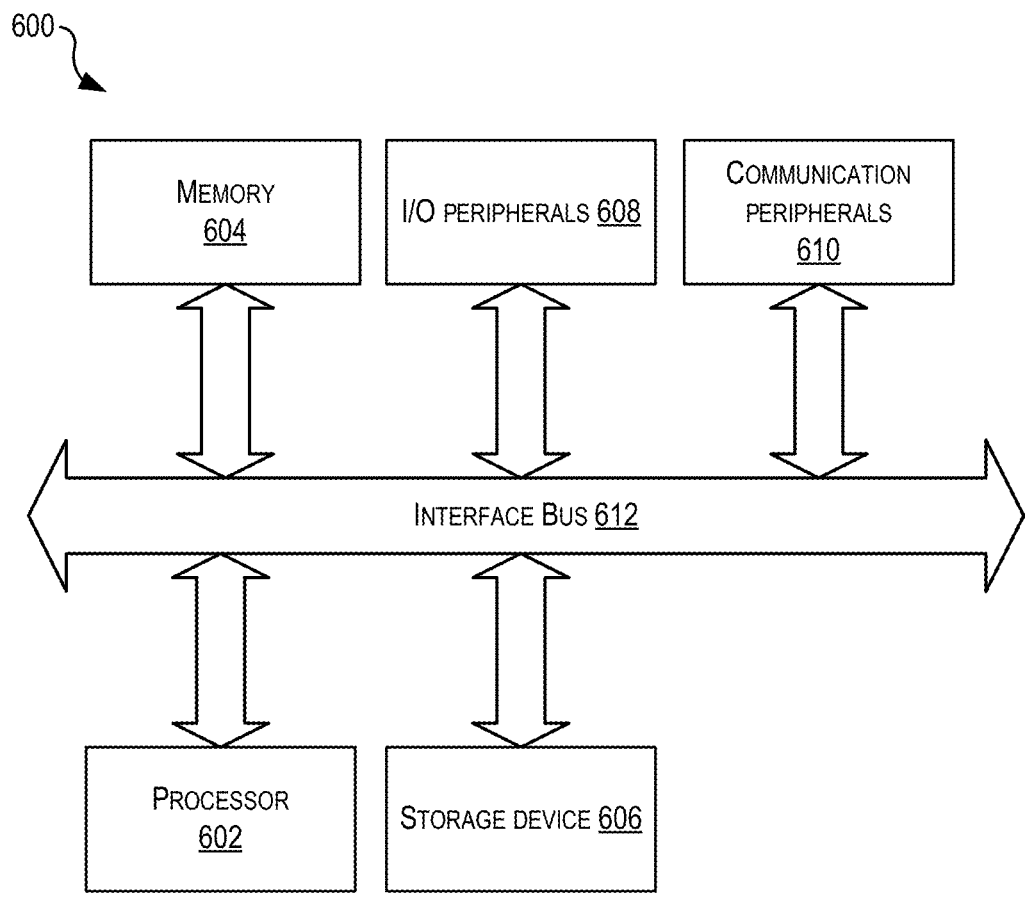
FIG. 6 illustrates an example system for implementing techniques relating to classifying insects, according to at least one example.

FIG. 6 illustrates examples of components of a computer system 600, according to at least one example. The computer system 600 may be a single computer such as a user computing device and/or can represent a distributed computing system such as one or more server computing devices. The computer system 600 is an example of the computing device 102. The computer system 600 may implement the management module 344 for managing aspects of the insect sortation system 100.

The computer system 600 may include at least a processor 602, a memory 604, a storage device 606, input/output peripherals (I/O) 608, communication peripherals 610, and an interface bus 612. The interface bus 612 is configured to communicate, transmit, and transfer data, controls, and commands among the various components of the computer system 600. The memory 604 and the storage device 606 include computer-readable storage media, such as Radom Access Memory (RAM), Read ROM, electrically erasable programmable read-only memory (EEPROM), hard drives, CD-ROMs, optical storage devices, magnetic storage devices, electronic non-volatile computer storage, for example Flash® memory, and other tangible storage media. Any of such computer-readable storage media can be configured to store instructions or program codes embodying aspects of the disclosure. The memory 604 and the storage device 606 also include computer-readable signal media. A computer-readable signal medium includes a propagated data signal with computer-readable program code embodied therein. Such a propagated signal takes any of a variety of forms including, but not limited to, electromagnetic, optical, or any combination thereof. A computer-readable signal medium includes any computer-readable medium that is not a computer-readable storage medium and that can communicate, propagate, or transport a program for use in connection with the computer system 600.

Further, the memory 604 includes an operating system, programs, and applications. The processor 602 is configured to execute the stored instructions and includes, for example, a logical processing unit, a microprocessor, a digital signal processor, and other processors. The memory 604 and/or the processor 602 can be virtualized and can be hosted within another computing system of, for example, a cloud network or a data center. The I/O peripherals 608 include user interfaces, such as a keyboard, screen (e.g., a touch screen), microphone, speaker, other input/output devices, and computing components, such as graphical processing units, serial ports, parallel ports, universal serial buses, and other input/output peripherals. The I/O peripherals 608 are connected to the processor 602 through any of the ports coupled to the interface bus 612. The communication peripherals 610 are configured to facilitate communication between the computer system 600 and other computing devices over a communications network and include, for example, a network interface controller, modem, wireless and wired interface cards, antenna, and other communication peripherals.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multipurpose microprocessor-based computing systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

What is claimed is:

1. An insect sortation system, comprising:
   an insect pathway defining an interior volume having an inlet and an outlet, wherein an approach zone of the insect pathway is defined adjacent the inlet, a classification zone of the insect pathway is defined adjacent the outlet, and a singulation zone of the insect pathway is defined between the approach zone and the classification zone;
   a puff back region defined adjacent the inlet;
   a puff forward region defined adjacent the outlet; and
   an imaging system disposed adjacent the insect pathway and configured to image insects on the insect pathway, wherein the puff back region is disposed between the inlet and the imaging system, and is configured to blow the insects away from the imaging system and toward the inlet.

2. The insect sortation system of claim 1, further comprising:
   a computing device comprising a memory and a processor configured to:
   receive image data from the imaging system; and
   determine positions of at least some of the insects on the insect pathway based on the image data.

3. The insect sortation system of claim 2, wherein the computing device is further configured to classify one or more insects when the one or more insects are in the classification zone.

4. The insect sortation system of claim 2, wherein each of the puff back region and the puff forward region comprises a puff system that comprises:
   one or more puff outlets extending within the respective region;
   an air source that provides an air flow to the one or more puff outlets; and
   a control valve disposed between the air source and the one or more puff outlets, and that controls the air flow to the one or more puff outlets.

5. The insect sortation system of claim 4, wherein the computing device is further configured to control the control valve in each puff system based on the positions of the insects to separate a single insect from the insects when the insects are in the singulation zone.

6. The insect sortation system of claim 1, wherein the insect pathway defines a rectangular cross section, with a height and a width selected to correspond to a representative insect of the insects.

7. The insect sortation system of claim 1, wherein the puff forward region is configured to blow insects toward the outlet.

8. The insect sortation system of claim 1, further comprising a shutter disposed within the singulation zone, the shutter comprising a track and a door that is moveable between an open state and a closed state.

9. The insect sortation system of claim 8, wherein, when the door is in the open state, the insects can freely move along the insect pathway.

10. The insect sortation system of claim 8, wherein, when the door is in the closed state, the insects are prohibited from moving along the insect pathway.

11. The insect sortation system of claim 8, wherein, when the door is in the closed state, the interior volume is divided into a first volume and a second volume.

12. The insect sortation system of claim 1, wherein the insect pathway comprises:
a floor on which the insects move;
a ceiling disposed above the floor; and
a pair of walls extending between the floor and the ceiling.

13. The insect sortation system of claim 12, wherein the floor is formed from a translucent material.

14. The insect sortation system of claim 13, further comprising one or more lighting elements disposed below the floor and positioned to provide light through the translucent material.

15. The insect sortation system of claim 12, wherein the ceiling is formed from a transparent material.

16. The insect sortation system of claim 1, wherein:
the imaging system is a position tracking imaging system configured to capture images of the insects for position tracking of the insects along the insect pathway; and
the insect sortation system further comprises an insect classification imaging system configured to capture images of the insects for classification of the insects within the classification zone.

17. An insect sortation method, comprising:
receiving image data from an imaging system disposed adjacent to an insect pathway, the image data representative of one or more insects on the insect pathway, the insect pathway comprising an inlet and an outlet;
determining positions of one or more insects with respect to a plurality of zones of the insect pathway based on the image data; and
causing movement, by a puff system disposed between the inlet and the imaging system, of at least one insect of the one or more insects based on a position of the at least one insect with respect to the plurality of zones, wherein causing the movement of the at least on insect comprises instructing the puff system to puff a burst of air that moves the at least one insect away from the imaging system and toward the inlet.

18. The insect sortation method of claim 17, wherein the imaging system comprises one or more cameras.

19. The insect sortation method of claim 17, wherein the plurality of zones comprise an approach zone disposed adjacent to the inlet of the insect pathway, a classification zone disposed adjacent to the outlet of the insect pathway, and a singulation zone disposed between the approach zone and the classification zone.

20. The insect sortation method of claim 19, wherein causing the movement, by the puff system, of the at least one insect further comprises instructing the puff system to puff the burst of air based at least in part on determining that the at least one insect has remained within the approach zone beyond a maximum amount of time.

21. The insect sortation method of claim 19, wherein causing the movement, by the puff system, of the at least one insect further comprises instructing the puff system to puff the burst of air based at least in part on determining that a quantity of insects within the approach zone exceeds a maximum quantity of insects for the approach zone.

22. The insect sortation method of claim 19, wherein the puff system is a first puff system and the burst of air is a first burst of air, the method further comprising causing movement, by a second puff system, of a different insect by at least:
determining that the different insect has remained within the classification zone beyond a maximum amount of time; and
instructing the second puff system to puff a second burst of air that moves the different insect toward the outlet.

23. The insect sortation method of claim 19, wherein the puff system is a first puff system and the burst of air is a first burst of air, the method further comprising causing movement, by a second puff system, of a different insect by at least:
determining that a quantity of insects within the classification zone exceeds a maximum quantity of insects for the classification zone; and
instructing the second puff system to puff a second burst of air that moves the insects toward the outlet.

24. The insect sortation method of claim 19, wherein causing the movement, by the puff system, of the at least one insect comprises isolating the at least one insect from the one or more insects.

25. The insect sortation method of claim 19, wherein:
the imaging system comprises one or more cameras; and
the method further comprises:
receiving additional image data from the imaging system when the at least one insect is located within the classification zone;
identifying one or more characteristics of the at least one insect based on the additional image data; and
classifying the at least one insect based on the one or more characteristics.

26. The insect sortation method of claim 25, wherein the one or more characteristics comprise a head, a body area, a body length, a tail, or an antenna.

27. The insect sortation method of claim 25, wherein classifying the at least one insect comprises classifying the at least one insect based on sex, health, species, genius, or size.

28. The insect sortation method of claim 25, further comprising causing movement, by the puff system, of the at least on insect based on classifying the at least one insect.

29. A non-transitory computer-readable storage device comprising computer-executable instructions that, when executed by a computer system, cause the computer system to perform operations comprising:
receive image data from an imaging system disposed adjacent to an insect pathway, the image data representative of one or more insects on the insect pathway, the insect pathway comprising an inlet and an outlet;
determine positions of one or more insects with respect to a plurality of zones of the insect pathway based on the image data; and
causing movement, by a puff system disposed between the inlet and the imaging system, of at least one insect of the one or more insects based on a position of the at least one insect with respect to the plurality of zones, wherein causing the movement of the at least on insect comprises instructing the puff system to puff a burst of air that moves the at least one insect away from the imaging system and toward the inlet.

30. The non-transitory computer-readable storage device of claim 29, wherein the plurality of zones comprise an approach zone dispose adjacent the inlet of the insect pathway, a classification zone disposed adjacent the outlet of the insect pathway, and a singulation zone disposed between the approach zone and the classification zone.

31. The non-transitory computer-readable storage device of claim 30, wherein causing the movement, by the puff system, of the at least one insect further comprises instructing the puff system to puff the burst of air based at least in part on determining that the at least one insect has remained within the approach zone beyond a maximum amount of time.

32. The non-transitory computer-readable storage device of claim 30, wherein causing the movement, by the puff system, of the at least one insect further comprises instructing the puff system to puff the burst of air based at least in part on determining that a quantity of insects within the approach zone exceeds a maximum quantity of insects for the approach zone.

33. The non-transitory computer-readable storage device of claim 30, wherein the puff system is a first puff system and the burst of air is a first burst of air, the computer-readable storage device comprising additional computer-executable instructions that, when executed by the computer system, cause the computer system to perform additional operations comprising causing movement, by a second puff system, of a different insect by at least:
  determining that the different insect has remained within the classification zone beyond a maximum amount of time; and
  instructing the second puff system to puff a second burst of air that moves the different insect toward the outlet.

34. The non-transitory computer-readable storage device of claim 30, wherein the puff system is a first puff system and the burst of air is a first burst of air, the computer-readable storage device comprising additional computer-executable instructions that, when executed by the computer system, cause the computer system to perform additional operations comprising causing movement, by a second puff system, of a different insect by at least:
  determining that a quantity of insects within the classification zone exceeds a maximum quantity of insects for the classification zone; and
  instructing the second puff system to puff a burst of air that moves the different insect toward the outlet.

35. The non-transitory computer-readable storage device of claim 30, wherein causing the movement, by the puff system, of the at least one insect comprises isolating the at least one insect from the one or more insects.

* * * * *